United States Patent
List et al.

(10) Patent No.: US 8,267,949 B2
(45) Date of Patent: Sep. 18, 2012

(54) FLEXIBLE DEVICE FOR INTRODUCING A MEDICAL APPARATUS INTO A BODY

(75) Inventors: Hans List, Hesseneck-Kailbach (DE); Otto Fuerst, Viernheim (DE); Hans-Peter Haar, Wiesloch (DE); Ulrich Haueter, Grosshoechstetten (CH); Herbert Harttig, Neustadt (DE); Johannes Pill, Leimen (DE)

(73) Assignees: Roche Diagnostics International AG, Steinhausen (CH); Roche Diagnostics Operations, Inc., Indianapolis, IN (US)

( * ) Notice: Subject to any disclaimer, the term of this patent is extended or adjusted under 35 U.S.C. 154(b) by 221 days.

(21) Appl. No.: 12/341,088

(22) Filed: Dec. 22, 2008

(65) Prior Publication Data

US 2009/0182289 A1    Jul. 16, 2009

(30) Foreign Application Priority Data

Jun. 22, 2006  (EP) .................................... 06012816

(51) Int. Cl.
    *A61B 17/32* (2006.01)
(52) U.S. Cl. ......................................................... 606/170
(58) Field of Classification Search .................. 606/170; 604/22, 115, 164.01, 164.03, 164.06, 523, 604/524, 525, 528, 531; 600/184
    See application file for complete search history.

(56) References Cited

U.S. PATENT DOCUMENTS

| | | | |
|---|---|---|---|
| 4,306,563 A * | 12/1981 | Iwatschenko | 604/265 |
| 4,490,465 A | 12/1984 | Limbach et al. | |
| 4,580,551 A | 4/1986 | Siegmund et al. | |
| 4,799,495 A | 1/1989 | Hawkins et al. | |
| 5,055,101 A * | 10/1991 | McCoy | 604/528 |
| 5,441,499 A | 8/1995 | Fritzsch | |
| 5,919,199 A | 7/1999 | Mers Kelly et al. | |
| 5,997,817 A | 12/1999 | Crismore et al. | |
| 6,102,886 A | 8/2000 | Lundquist et al. | |
| 6,743,239 B1 | 6/2004 | Kuehn et al. | |
| 6,814,844 B2 | 11/2004 | Bhullar et al. | |
| 6,890,329 B2 * | 5/2005 | Carroll et al. | 604/528 |
| 2001/0047138 A1 | 11/2001 | Kokate et al. | |
| 2005/0075644 A1 | 4/2005 | DiPoto et al. | |
| 2005/0201897 A1 | 9/2005 | Zimmer et al. | |
| 2006/0064037 A1 | 3/2006 | Shalon et al. | |
| 2006/0100575 A1 | 5/2006 | Restelli et al. | |
| 2006/0100582 A1 | 5/2006 | Marianowicz et al. | |
| 2006/0100583 A1 | 5/2006 | Terzoli | |

FOREIGN PATENT DOCUMENTS

| | | |
|---|---|---|
| DE | 4243715 C2 | 7/1994 |
| EP | 1459691 A1 | 9/2004 |
| WO | 03/080169 A1 | 10/2003 |
| WO | 2004/052594 A2 | 6/2004 |
| WO | 2005/044116 A2 | 5/2005 |
| WO | 2006/061354 A1 | 6/2006 |

* cited by examiner

*Primary Examiner* — Ryan Severson
*Assistant Examiner* — Jonathan W Miles
(74) *Attorney, Agent, or Firm* — Harness, Dickey

(57) ABSTRACT

An introducing device for introduction of a medical device into a body is described which has a distal region with a tip region for generating an opening in the skin, and a segment region which comprises at least two sections which, in a rigid state, are essentially rigidly connected at least to one another and to the distal region and which are movable relative to one another in a flexible state. Furthermore, a system is described in which a sensor is integrated into the device for introduction into a body.

24 Claims, 4 Drawing Sheets

FLEXIBLE DEVICE FOR INTRODUCING A MEDICAL APPARATUS INTO A BODY

REFERENCE

This application is a continuation of PCT/EP 2007/005468 filed Jun. 21, 2007 which is based on and claims priority to European Patent Application No. EP 06 012 816.2 filed Jun. 22, 2006, which are hereby incorporated by reference.

FIELD

The disclosure concerns a device for introducing a medical device into a body the flexibility of which is different before and after the puncture.

Devices for puncturing have a wide variety of uses in the field of medicine especially for transcutaneous or subcutaneous administration. In the diagnostic field needles and blades which are suitable for generating a small skin opening that are not too deep are mainly used. Since they are only used for puncturing, they usually have a solid and rigid structure. Cannulas which are characterized in that they are hollow inside and therefore allow a flow of fluids can be used in the therapeutic field.

BACKGROUND

In a large number of therapeutic or diagnostic applications, it is necessary to implant a device such as a cannula for a long period in the body tissue. This is often necessary in order to for example enable therapeutic or diagnostic fluids to be administered repeatedly or for a long period. In doing so the problem occurs that the device must have a certain rigidity to enable puncturing and, on the other hand, it should be flexible in order to avoid injury when the patient moves.

Catheters are known from the documents US 20060100582 and US 20060100583 which are used to introduce a cannula into the body in order to for example administer drugs. In this case the catheter consists of a stiff or hard material for insertion into the body. The puncturing, pointed part of the catheter is removed after insertion into the body in order to avoid injury. The cannula can consist of a soft material so that it can adapt to movements.

The catheters of US 20060100582 and US 20060100583 have the disadvantage that the catheter is only used to puncture the body and does not have any further function after introduction into the body. Conversely, the cannula is not suitable for puncturing because it consists of a material whose shape adapts to the body and is not adapted to the forces of a puncture. Due to the invariable hardness of the catheter and the cannula, at least two elements are necessary to introduce a device into a body. One element for puncturing and a further element for the medical treatment.

SUMMARY

Embodiments of the invention provide a device for introducing a medical device (e.g. a cannula or a sensor) into a body which is simple to handle and enables a problem-free penetration of the body and reduces injuries during the period in which it is carried in the body.

One embodiment of the invention describes a device for introducing a medical device into a body which is referred to in the following as an introducing device and has a distal region which has a tip region for generating an opening in the skin, and a region which comprises at least two sections which are connected at least to one another and to the distal region in an essentially rigid manner in a rigid state and which can move relative to one another in a flexible state.

A medical device can be introduced into the body with the aid of the introducing device because the introducing device is suitable for insertion into the body in its rigid state. The medical device can be a therapeutic device such as for example a cannula for administering therapeutic agents or a diagnostic device such as for example a sensor for analysing analytes in the body fluid. In this case the introducing device can be connected to the medical device in such a manner that they do not have to be separated from one another; i.e., they form a unit. Various embodiments of the introduction of diagnostic devices and sensors is described in detail in the following.

The introducing device can have an elongated dimension in order to cause as little pain as possible when it penetrates the skin. Furthermore, the elongate device can have a round shape in cross-section. The device has at least two regions. One of these regions is the distal region with a needle tip. A further region is the segment region which in turn consists of at least two sections. These at least two sections are connected to one another and to the distal region. The at least two sections which are also referred to as the segment region can be present in two different states. In a first state the at least two sections are rigidly connected together while they can move relative to one another in a second flexible state. Since the sections are also connected together in their flexible state, they can move relative to one another. In the flexible state the movement of the sections can be compared with the movement of a snake which can also move sections of its body transversely to their alignment while the sequence of the sections remains unchanged. The rigid, i.e., inflexible state can for example be brought about by compressing the device such as occurs for example during the puncture or by a forming element. When the device is inserted into the body, the surface of the body forms a resistance which is sufficient to press the segments together and to shift the device into the rigid or inflexible state. After the device has been inserted into the body, the resistance is overcome and no compressive forces act any longer on the sections or segments.

In addition, the rigid state can be achieved by the forming element. The forming element can for example be a binding agent. This binding agent can be at least partially water-soluble and can be dissolved or degraded in the body. Alternatively the forming element can also be a connecting element which holds the sections together. The at least two sections can consist of several coils like a spring and can consist of segments of various shapes such as for example rings or cylinders.

Shortly before the puncture the introducing device is in the rigid state. In this rigid state the introducing device is so rigid that it can be inserted into the body without being bent sideways. After the introducing device has penetrated the body, the device is converted into the flexible state in the region which consists of the at least two sections. This can either take place actively by releasing the tension of for example a pull wire or passively by dissolution of for example the immobilizing agent. The mobility of the device in the inserted state is for the comfort of the patient who can carry this device in his body over a longer period of several days. The movable sections enable the device to adapt to the movements of the patient and thus reduce injury in the tissue. The aim is not to traumatize the tissue around the device. In addition to the comfort for the patient, the low degree of traumatization of the tissue has the advantage that metabolic processes of the body at the puncture site are not significantly changed compared to the normal state and thus a representative state is present. This unimpaired tissue state is a prerequisite for a reproducible and representative measurement of analytes in the tissue.

The medical device can interact with the tissue can be permanently connected to the introducing device or the introducing device and the medical device may be loosely connected. In this case the connection can be released or made at any time before or after the puncture and thus the two devices are separated from one another or brought together. In one embodiment, a sensor for analysis in the tissue fluid is permanently connected to the introducing device.

In order to further improve the compatibility and comfort for the patient, a membrane can be additionally placed over the at least two sections. This membrane should prevent tissue from being pinched between the at least two sections that move relative to one another when the device is in its flexible state. Furthermore, the membrane can ensure the functionality of a medical device inserted into the device because the membrane can also be used as a protection against the penetration of large molecules. This membrane can be very thin and in addition flexible and biocompatible.

In another embodiment of the system, at least one part of the device is hollow. Furthermore, the system can have a sensor. The sensor can be located in the hollow region of the device. In order to contact the sensor, the device has a contact element. If the tip region is hollow, the sensor can also be located in the hollow tip region. In this case the sensor consists of at least two electrodes whose active areas are coated with an enzyme which serves to detect the analyte as is known from the U.S. Pat. Nos. 5,997,817 and 6,814,844. The electrodes are for example contacted via the proximal end of the device in order to ensure current supply and data transfer. Current supply and the data transfer can be integrated into the system but can also be arranged outside the introducing device and coupled to the system via contacts.

The analyte concentration which is for example shown to the patient on a display can be calculated from the electrical data of the sensor in an evaluation unit. This evaluation and/or display unit can be directly integrated on the device for insertion into a body or it can be coupled thereto as required. The device can, however, also be provided with a data transfer device which transmits the electrical data to an evaluation unit. This evaluation unit can for example be located together with a display unit in a device which the patient carries at a different position on his body (for example a watch) or which he carries as a hand-held instrument (such as for example an organizer, mobile telephone or other small electronic instruments).

In addition the puncturing device can comprise a device for removing the puncturing device from the body of a patient. This can for example be a thread made from a material such as steel or nylon which is attached to the puncturing device. This device can be connected to the tip of the puncturing device in order not to pinch tissue parts in the gaps between the sections.

Tip Region

As already mentioned, the tip region is located in the distal region of the device. This region is used to introduce the device into the skin in a painless manner. The sidewalls converge in this region and end in a tip. In a one embodiment the tip is suitable for an atraumatic insertion into the body as is known for acupuncture needles. The material of this tip is suitable for withstanding the forces which occur during insertion into a body. This can for example be ensured by using materials such as ceramic, metal or plastic or combinations thereof. Suitable metals are especially tissue-compatible steels containing Cr, Ni, CoCr or titanium alloys. The ceramics can be based on aluminium oxide or zirconium oxide. When using plastics polysulfones, polyamides or PEEK™ are for example particularly suitable. In this connection the tip can also be hollow on the inside as is the case for a cannula. The flexible region, which is also referred to as the segment region, which can consist of different materials than the tip adjoins the tip region which can be several millimeters in length, such as from 1 mm to 4 mm in length.

Sections/Segments

The segment region consists of at least two sections. These sections can contain segments which can consist of different materials or mixtures thereof such as for example fabric, ceramic, plastic or metal. The segments can have a wide variety of forms such as for example the form of a spring in which the sections merge into one another without a discontinuity or rings or cylinders which lie flat on top of one another or have edges which hook into one another. The individual sections are connected together such that they can move relative to one another but cannot slip apart. This flexible connection can for example be a hooking together of the segments. This for example corresponds to the principle of a link chain. The segments can be hollow inside or they can be solid. Their size and dimensions can vary. The length of the segment region can vary greatly depending on the field of application of the introducing device. In a some embodiments, the segment region which can additionally contain a sensor region can be between 5 mm and 30 mm in length.

Membrane

The segment region can be covered with biocompatible coatings or it can itself be biocompatible because it remains for several days in the body of a patient. Alternatively or in addition, a membrane which can have several functions (such as for example the biocompatibility) can be pulled over the segments. The membrane prevents enzymes and other reagents from escaping from the sensor region and at the same time prevents penetration of components (such as large proteins, cells or cell components) from the blood and/or the tissue fluid into the sensor region. Such components can have a major effect on the stability and functionality of the sensor region and should therefore be kept away from the sensor region. The membrane which is optionally pulled over the movable sections can consist of adequately firm or flexible, biocompatible materials. These are for example materials which are used as (micro) dialysis membranes, such as cellulose (regenerated) or cellulose derivatives (including for example acetate-substituted or diethylaminoethyl-substituted cellulose). Furthermore, synthetic polymers such as polysulfones, polymethacrylate (PMMA), polyacrylonitrile, polyacrylic ether sulfone or copolymers thereof are suitable, as are membranes based on polysiloxanes or modified polyurethanes and other polymers.

Forming Element

The forming element can be used to immobilize the at least two sections and thus make them rigid. In this connection, the forming element can have different designs. The forming element can be brought into at least two different states. The forming element can adopt one state before the device is introduced and adopts the other state after the device has been introduced. In the one state the at least two sections are rigid and in the other state the at least two sections have a flexible arrangement. If the forming element is solid such as for example in the form of a wire or a clip, it can bring the sections into the rigid or flexible state at any time before or after introducing the device into the body. This type of forming element is referred to in the following as a connecting element.

Alternatively the forming element can also be positioned in, on or between the sections and change its shape after introducing the device into the body such that it can no longer immobilize the sections. This type of forming element can for example be an immobilizing agent.

Immobilizing Agent

The immobilizing agent which may be introduced into, onto or between the sections in order to convert the device into the rigid state, locks at least some of the sections together (such as the segment region, distal region, proximal region, sensor region etc.). The immobilizing agent has an adequate hardness outside the body in order to sufficiently immobilize the sections when the device is inserted into the body. In the inserted state the immobilizing agent should at least partially dissolve in the body and thus enable the movement of the sections or segments relative to one another. A change in the mobility of the immobilized sections can be caused by the partial or complete dissolution of the immobilizing agent, swelling/softening of the immobilizing agent, or biodegradable polymers. For partial or complete dissolution of the immobilizing agent, at least a part of the immobilizing agent consists of a low-molecular component which dissolves in the tissue fluid or in water and thus abolishes the rigid structure of the immobilized sections. For swelling/softening of the immobilizing, tissue fluid or water swells the immobilizing agent or softens it, and the immobilizing agent thus loses its rigidity. Polymers of hydroxymethylmethacrylate (in PHEMA) are for example suitable for this. Cross-linked, water-swellable polymers can be used for the softening such as polyacrylic acids or starch derivatives as well as fats or parafins. For biodegradable biopolymers, hydrolysis-sensitive polymers which have a high stability in the dry state and are degraded in a suitable environment (such as in tissue fluid). These polymers for include polyglycolic acid, D, L-polylactic acid or derivatives and/or copolymers thereof.

These methods and components can also be combined with one another in order to achieve the greatest possible tolerability for the patient and change the composition of the tissue fluid as little as possible.

Salts can be used as soluble materials and crystallizing salts such as NaCl, Na lactate or organic compounds such as sugars which form compression-resistant crystals which are sufficient to stiffen the introducing device. Alternatively it is also possible to use glass-like materials such as e.g. sugar glass. Crystallizing materials can be introduced into the interspaces of the introducing device in the form of saturated or super-saturated solutions where crystals are formed in the interspaces due to the evaporation of the solvent. An example of such a sugar glass solution is a mixture of cane sugar and water in a ratio of 4.9:1. The mixture is heated until a homogeneous paste is formed. The flexible sections of a puncturing device are at least partially immersed in the hot paste and excess material is scraped off.

The softening materials can either be introduced into the sections as a solution in a non-aqueous solvent or a water-soluble precursor of the material is introduced into the sections and cross-linked or chemically modified therein in such a manner that the material loses its water-solubility.

If the sections for example consist of the twists of a woven or twisted fabric, then an immobilizing agent can be introduced into or onto the fabric as a stabilizing substance which makes the sections rigid before the device is inserted into the body and which dissolves and/or swells after the device has been introduced into the body as described above and makes the device flexible towards movements of the patient. This immobilizing agent can also be applied under, into or onto a membrane as already described above in order to achieve this stabilizing effect. Alternatively a liquid such as for example water can be used as an immobilizing agent which is iced before introducing the device into the body and dissolves or melts there after the device has been introduced into the body.

Connecting Element

As already mentioned connecting elements which are insoluble in water and essentially do not change this property before and after introduction of the device into the body, can also be used to immobilize the sections. In this case, the sections can be held together by a clip which can be tensioned or released as required. Alternatively the sections can also be pulled together by one or more magnets whose magnetic effect can be controlled by electricity. One embodiment of the connecting element is a pull wire which serves to loosely connect the sections in the flexible state and to firmly connect the sections in the rigid state. In order to rigidly connect the sections together, the pull wire must be shortened or tightened which can for example be achieved by mechanical or electrical means. When the pull wire is shortened mechanically, the pull wire can be tightened by the patient himself or by an additional element such as for example a butterfly. A butterfly is an aid for injecting needles in order to ensure a comfortable handling as is known in the prior art and described in the US Patent application US 20060100575. For this purpose the pull wire can be manufactured from any material which enables it to be tightened (and loosened again) in such a manner that the pull wire does not tear. If the pull wire is electrically shortened, a material can be used which changes its dimensions when current is applied. This can be achieved by a metal alloy such as for example one made of Ti/Ni. This alloy contracts when current is applied and expands again after the current supply is terminated and adopts its original flexible form again. A pull wire can be used when the sections consist of essentially rigid segments. The pull wire can be composed of various materials which can be connected to different regions of the device. These may be different plastics but also metal and/or metal alloys.

Sensors

As already described the sensor can be directly integrated into the introducing device or be coupled to this device. The sensor can be located at any positions of the introducing device which are in contact with body fluid after the device has been introduced into the body. If it is loosely connected to the introducing device, then at least a region of the introducing device should be hollow inside in order to insert the sensor.

If the sensor is permanently connected to the introducing device as is the case in some embodiments, the introducing device does not have to have a hollow space but rather the sensor is attached in or on the device such that an adequate liquid exchange with the tissue fluid can take place.

In one embodiment, the sensor region is in the interior of the introducing device. In order to ensure a liquid exchange of the sensor with the surrounding liquid, perforations can be introduced into the wall of the introducing device in order to ensure an adequate liquid exchange with the tissue fluid. This has the advantage that the sensor can be easily contacted and is protected from mechanical effects outside of the introducing device. A rapid liquid exchange is ensured by adequately large perforations.

Alternatively the sensor region can be located on the outside of the introducing device and optionally be protected by a membrane. This has the advantage that the sensor region can directly make contact with the liquid and the liquid exchange is not delayed by diffusion processes (apart from a membrane which may be present).

The sensor can be used to measure physical conditions such as temperature and pressure and/or chemical conditions or concentrations and be based on various measuring principles. Resistive, amperometric or calorimetric sensors can be used. Galvanic, capacitive, inductive or other sensors are also conceivable. It is, however, also possible to carry out an optical measurement by introducing light guides. In addition to a direct detection of the analyte e.g. on an optical basis, it is also possible to measure the analyte by means of a reagent which requires that the analyte reacts with the reagent such as e.g. an enzyme. Such reactions are well-known in the prior art as described in U.S. Pat. No. 4,490,465 and US 20050201897.

The current source for the sensor can be a rechargeable battery which can be inductively charged and is integrated into parts of the introducing device. However, the current source can also be located outside of the introducing device and only be connected to it when in use.

Furthermore, the electronics for controlling the sensor can be located in the introducing device. This can be a microprocessor for control and data processing as well as an active transmitter unit to transmit compressed data and/or a passive radio unit such as an RFID (radio frequency identification) unit for data transfer as is known in the prior art (US 20060064037). The data processing and/or transmission can, however, also take place outside the introducing device.

BRIEF DESCRIPTION OF THE DRAWINGS

FIG. 2a shows a magnified diagram of the segment region from FIG. 1 in a rigid state.

FIG. 2b shows a diagram of the segment region from FIG. 1 in the flexible state.

DETAILED DESCRIPTION

Figure 1:
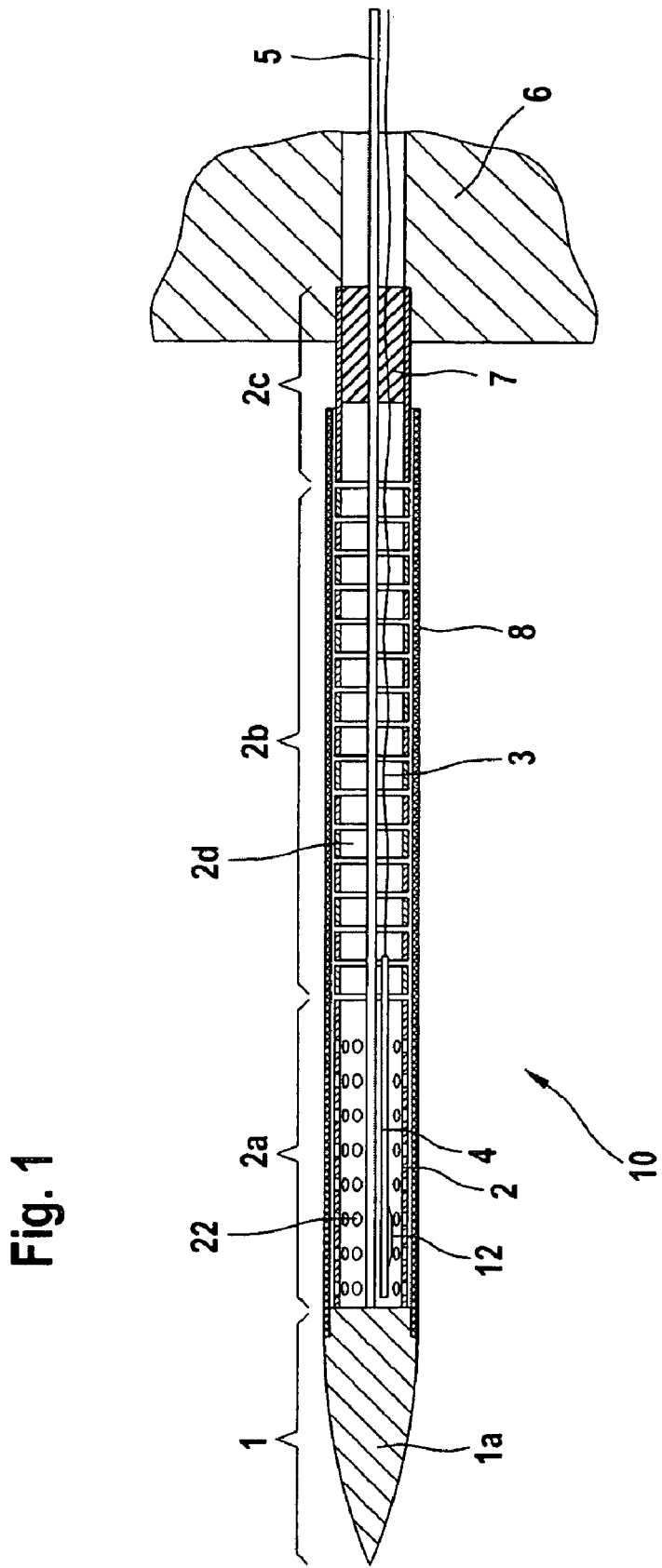
FIG. 1 shows a diagram of a device for introduction into a body that comprises a needle tip, sensor region, segment region and proximal region.

FIG. 1 shows a device 10 for introduction into a body. The distal region with 1a needle tip 1a is located at the distal end of the device 10. A segment region 2 which can be manufactured from the same or a different material than the needle tip 1a adjoins this needle tip 1a. This segment region 2 comprises a sensor region 2a which is placed in the segment region 2, and adjoins the needle tip 1a. This sensor region 2a has perforations 22 in the casing in order to ensure liquid exchange with the tissue. Reagents 12 which react with the analyte and cause an electrically measurable change of the signal at the electrodes are applied to the sensor 4. The middle segment region 2b which merges into a proximal region 2c in the proximal part of the device 10, adjoins the sensor region 2a. This proximal region 2c can be a smooth tube. A liquid stop 7 is located in this proximal region 2c which prevents liquid from the middle segment region 2b from penetrating into the proximal region 2c. The liquid stop can be an elastomer. In addition this liquid stop 7 prevents germs from entering through the proximal region 2c of the device 10 into the segment region 2 or into the tissue. The device 10 is otherwise hollow inside between the needle tip 1a and the proximal region 2c. A lead 3 for the sensor 4 is located in the interior of the device 10. The entire length of the segment region 2 between the needle tip 1a and the proximal region 2c consists of individual segments 2d. These segments 2d adjoin the sensor region 2. The sensor region 2 is connected to a pull wire 5 which passes through the liquid stop 7 and is connected to other parts of the device 10. A membrane 8 which is permeable to the analyte and flexibly encloses the segments is located around the segment region 2.

Figure 2:
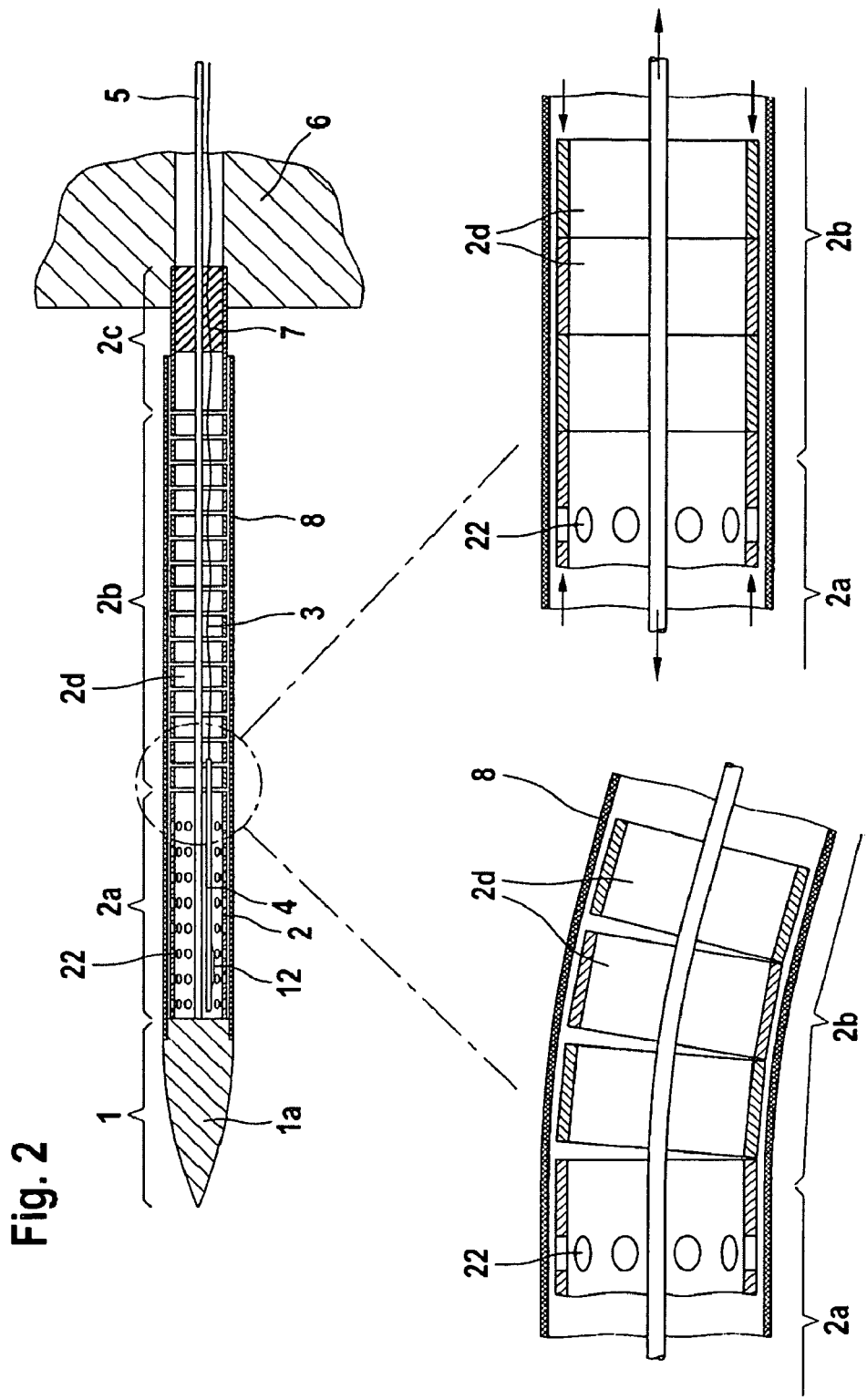
FIG. 2 shows a detail view of the device of FIG. 1.

The implanted part of the device 10 is also shown in FIG. 2, where FIG. 2a shows a section of the segment region 2 which is in the junction between the sensor region 2a and the middle segment region 2b. This segment region 2b is shown in its rigid state in FIG. 2a. The arrows show that the segments 2d can be pressed onto each other. This occurs by means of a force which is exerted on the pull wire 5 which is connected to at least two of the segments 2d. In order to achieve an optimal stiffening of the segments, the pull wire 5 is connected to the distal region 1 and to the proximal region 2c. The segments 2d are pressed onto each other by shortening the pull wire 5 in this region and the device is stiffened for the insertion 10. The same segment region as in FIG. 2a is shown in FIG. 2b where the pull wire 5 is not under tension so that the segments 2d can move relative to one another.

Figure 3:
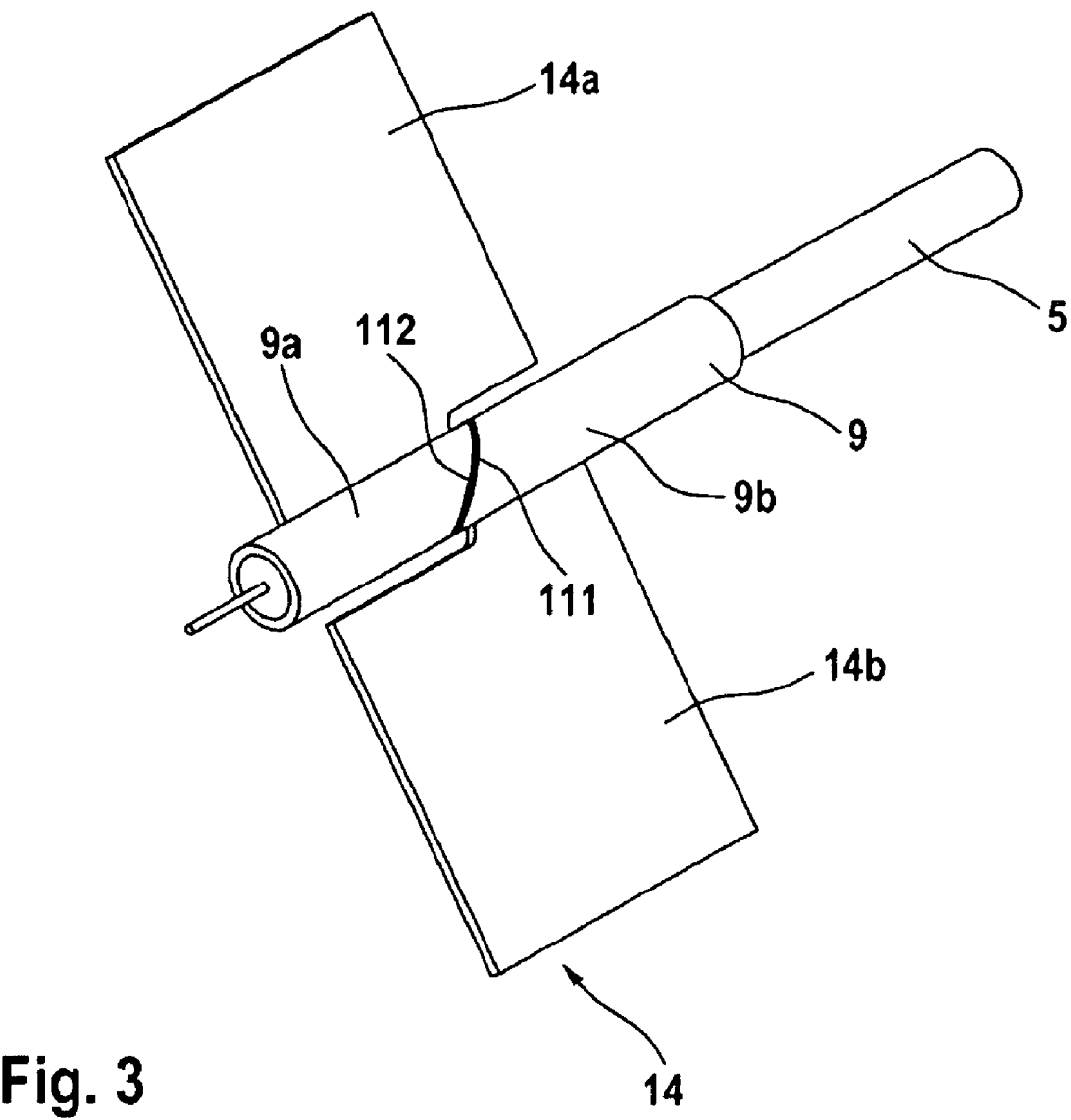
FIG. 3 shows a diagram of a pull device for tensioning the segment region from FIG. 1 in the form of a butterfly.

A method for tensioning the pull wire 5 from FIGS. 1 and 2 is shown in FIG. 3. For this purpose a so-called butterfly 14 is provided as a pull device. The inclined faces of the two wings 14a and 14b rest against one another, the so-called first lifting slope 111 and the second lifting slope 112, and are thus locked in position relative to one another such that they are always coaxial to each other.

The pull wire 5 is attached to the first wing 14a and the proximal part 2c of the segment region 2 is attached to the second wing 14b. When the wings 14a and 14b are rotated against one another, the lifting slopes 111 and 112 ensure that the two wings 14a and 14b must axially move apart. In this process the proximal region 2a of the segment region is pushed forwards, the distal region 1 with the tip 1a is pulled backwards by the pull wire 5. As a result the stack of segments 2b is subjected to a compressive force and the segments can no longer tilt relative to one another. As a result the complete mechanism behaves like a rigid rod.

Figure 4:
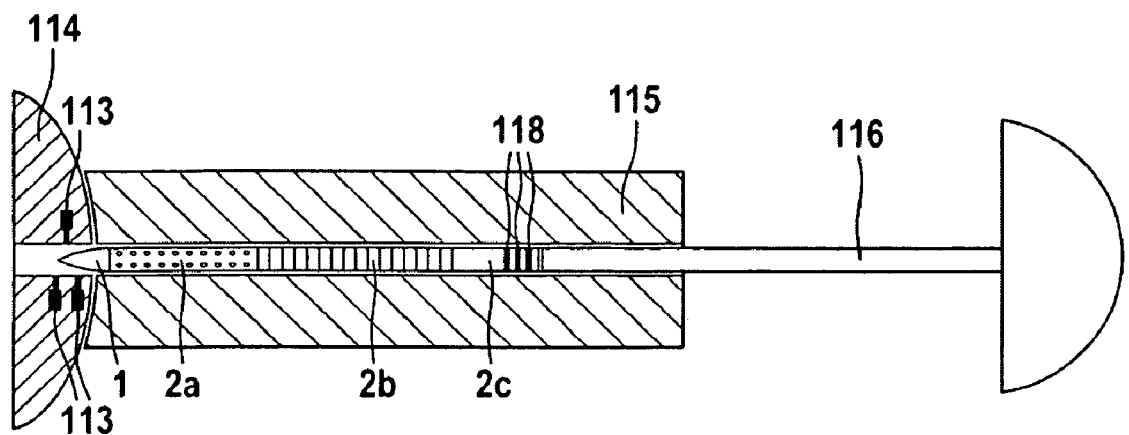
FIG. 4 shows a diagram of an insertion aid.
Figure 4A:
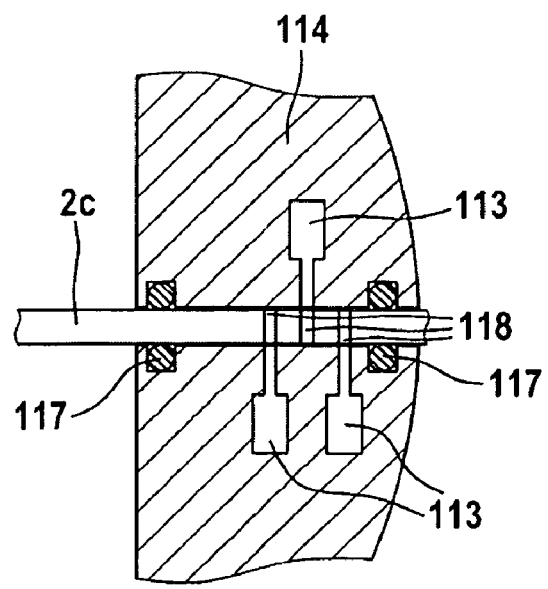
FIG. 4a shows a diagram of the proximal end of the device after insertion into the body.

FIG. 4 shows a device for introduction into a body comprising an integrated sensor region 2a, the segment region 2 and a contacting region 118 for electrically contacting the sensor. The proximal region 2c of the introducing device 10 is detachably connected to an applicator 116 which facilitates the insertion of the device 10. In order to ensure an adequate guidance of the device 10 during the insertion, the device 10 is placed in an insertion sleeve 115 which prevents bending or slipping of the device 10 when it is inserted into the body. A contacting element 114 which is attached to the skin surface is used to make contact with the contacting region 118 after the device 10 has been inserted into the body as shown in FIG. 4a. The electrical connections of the leads 3 from the sensor region 2a end in the contacting region 118 and are contacted by the contacts 113 of the contacting element 114. This contacting region 118 is protected from the penetration of liquid by sealing elements 117 which are located in the contacting element 114. A current source for supplying the sensor 4 can be present in the contacting element 114 as well as a transfer module for transferring data to a further instrument which is not shown here. Since the device 10 is supported externally during its application, no pull wire 5 is necessary in addition to the butterfly 14 to tension the butterfly 14 and thus the segments.

Thus, embodiments of the flexible device for introducing a medical apparatus into a body are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. An introducing device for introducing a medical device into a body, comprising:
a distal region which has a tip region structured to generate an opening in skin;
a segment region having more than two discontinuous sections that are essentially rigidly connected to at least one another and to the distal region in a first rigid, linear state for introducing the device and the more than two discontinuous sections are movable relative to one another in a flexible state after the device has been introduced, wherein the more than two discontinuous sections are rigidly connected to one another and to the distal region in the first rigid, linear state by an immobilizing agent and wherein the immobilizing agent is configured to dissolve or degrade into the body causing the more than two discontinuous sections to change from the first rigid, linear state to the flexible state.

2. The device according to claim 1, further comprising a forming element that is connected to more than one of the discontinuous sections and configured to selectively move the more than two discontinuous sections from a spaced apart position relative to each other into contact with each other in a second rigid state subsequent to the flexible state.

3. The device according to claim 1, wherein the device is hollow in at least one of a part of the distal region and at least in a part of the more than two discontinuous sections.

4. The device according to claim 1, wherein the more than two discontinuous sections consist of essentially rigid segments.

5. The device according to claim 4, wherein the more than two discontinuous sections are held together by a forming element.

6. The device according to claim 5, wherein the forming element is a pull wire.

7. The device according to claim 6, wherein the pull wire contracts when the temperature increases.

8. The device according to claims 6, wherein the pull wire is tightened by a pulling device.

9. The device according to claim 1, wherein the more than two discontinuous sections are covered with a membrane.

10. The device according to claim 9, wherein the membrane is permeable and flexible.

11. The device according to claim 9, wherein the membrane contains the immobilizing agent.

12. The introducing device of claim 1 wherein the more than two discontinuous sections comprises at least five discontinuous sections in the second rigid, linear state.

13. An introducing device for introducing a medical device into a body, comprising:
a distal region having a tip that is configured to generate an opening in skin;
a segment region having more than two discontinuous sections;
a flexible and permeable membrane that encloses the more than two discontinuous sections; and
a flexible member connected to at least one of the discontinuous sections and configured to move the more than two discontinuous sections from a spaced apart position relative to each other into abutting engagement with each other in a rigid, linear state upon advancement of the flexible member in a direction away from the distal region.

14. The introducing device of claim 13 wherein the more than two discontinuous sections are rigidly connected to one another and to the distal region by an immobilizing agent in a rigid state, wherein the immobilizing agent is configured to one of dissolve or degrade into the body causing the at least more than two sections to move from the rigid state to a flexible state.

15. The introducing device of claim 13 wherein the flexible member comprises a pull wire.

16. The introducing device of claim 15 wherein the pull wire contracts when the temperature increases.

17. The introducing device of claim 13 wherein the more than two discontinuous sections comprises at least ten discontinuous sections that are configured to collectively form a gradual radius within the membrane in a flexible state and are configured to collectively form a linear arrangement in the rigid, linear state.

18. The introducing device of claim 13, further comprising a sensor region disposed intermediate the distal region and the segment region, the sensor region configured to at least partially house the medical device at a position proximally relative to the distal region.

19. The introducing device of claim 13 wherein the more than two discontinuous sections are in a rigid, linear state along a majority of the segment region.

20. An introducing device for introducing a medical device into a body, comprising:
a distal region having a closed tip that is configured to generate an opening in skin;
a segment region having more than two discontinuous segments;
a sensor region disposed intermediate the distal region and the segment region, the sensor region configured to at least partially house the medical device at a position proximally relative to the distal region;
a flexible membrane that encloses the more than two discontinuous segments;
an immobilizing agent disposed on the more than two discontinuous segments that locks the more than two discontinuous segments from relative movement in a rigid, linear insertion state, the immobilizing agent configured to one of dissolve or degrade into the body causing the more than two discontinuous segments to be in a flexible state.

21. The introducing device of claim 20, further comprising a flexible member connected to more than one of the discontinuous segments and configured to move the more than two discontinuous segments together into a rigid, linear configuration upon advancement of the flexible member in a direction away from the distal region subsequent to the one of dissolving or degrading of the immobilizing agent into the body.

22. The introducing device of claim 20 wherein the flexible member comprises a pull wire.

23. The introducing device of claim 22 wherein the pull wire contracts when the temperature increases.

24. The introducing device of claim 20 wherein the more than two discontinuous segments comprises at least ten discontinuous segments that are configured to collectively form a gradual radius within the membrane in a flexible state and are configured to collectively form a linear arrangement in the rigid, linear configuration.

* * * * *